(12) United States Patent
Morita et al.

(10) Patent No.: US 10,835,140 B2
(45) Date of Patent: Nov. 17, 2020

(54) BIOLOGICAL ELECTRODE TOOL

(71) Applicant: TATSUTA ELECTRIC WIRE & CABLE CO., LTD., Osaka (JP)

(72) Inventors: Takashi Morita, Kyoto (JP); Keisho Shinohara, Kyoto (JP)

(73) Assignee: TATSUTA ELECTRIC WIRE & CABLE CO., LTD., Osaka (JP)

( * ) Notice: Subject to any disclaimer, the term of this patent is extended or adjusted under 35 U.S.C. 154(b) by 324 days.

(21) Appl. No.: 15/557,002

(22) PCT Filed: Mar. 3, 2016

(86) PCT No.: PCT/JP2016/056622
§ 371 (c)(1),
(2) Date: Sep. 8, 2017

(87) PCT Pub. No.: WO2016/143666
PCT Pub. Date: Sep. 15, 2016

(65) Prior Publication Data
US 2018/0055399 A1 Mar. 1, 2018

(30) Foreign Application Priority Data
Mar. 12, 2015 (JP) .................................. 2015-049026

(51) Int. Cl.
*A61B 5/0408* (2006.01)
*A61B 5/0478* (2006.01)
*A61B 5/00* (2006.01)

(52) U.S. Cl.
CPC .......... *A61B 5/0408* (2013.01); *A61B 5/0478* (2013.01); *A61B 5/04087* (2013.01); *A61B 5/6832* (2013.01)

(58) Field of Classification Search
CPC .................................................. A61B 5/0408
(Continued)

(56) References Cited

U.S. PATENT DOCUMENTS 4,082,086 A * 4/1978 Page .................. A61B 5/04085
600/391
4,082,087 A * 4/1978 Howson ............. A61B 5/04085
600/391
(Continued)

FOREIGN PATENT DOCUMENTS

JP 05036402 9/1993
JP 2013236922 11/2013
(Continued)

OTHER PUBLICATIONS

International Search Report dated May 31, 2016 filed in PCT/JP2016/056622.

*Primary Examiner* — Lee S Cohen
(74) *Attorney, Agent, or Firm* — Rankin, Hill & Clark LLP

(57) ABSTRACT

Provided is a biological electrode tool including an electrode portion (10) attached to a human body to acquire a biological signal, and a lead portion (20) for externally leading out the biological signal from the electrode portion (10). The entire areas of the upper and lower surfaces of the electrode portion (10) are covered with a nonwoven fabric (30) except for a portion that contacts the living body (13). The entire areas of the upper and lower surfaces of the lead portion (20) are also covered with nonwoven fabric except for an external lead-out end portion (14). The full circumferential peripheries of the nonwoven fabrics (30) on the upper and lower surfaces of the electrode portion (10) and the lead portion (20) are bonded except for the portion that contacts the living body (13) and the external lead-out end portion (14). Neither the electrode (11) of the electrode portion (10) nor a thin-film lead wire (21) of the lead portion (20) are exposed.

8 Claims, 6 Drawing Sheets

(58) Field of Classification Search
USPC .................................................. 600/391, 392
See application file for complete search history.

(56) References Cited

U.S. PATENT DOCUMENTS

| | | | | | |
|---|---|---|---|---|---|
| 4,353,372 | A | * | 10/1982 | Ayer | A61B 5/04085 174/117 FF |
| 4,370,984 | A | * | 2/1983 | Cartmell | A61B 5/04026 600/385 |
| 4,524,775 | A | * | 6/1985 | Rasmussen | A61B 5/0408 156/73.5 |
| 4,539,995 | A | * | 9/1985 | Segawa | A61B 5/0408 174/36 |
| 4,694,835 | A | * | 9/1987 | Strand | A61B 5/04087 600/385 |
| 4,763,660 | A | * | 8/1988 | Kroll | A61B 5/04085 439/77 |
| 5,024,227 | A | * | 6/1991 | Schmid | A61B 5/04087 600/391 |
| 5,450,845 | A | * | 9/1995 | Axelgaard | A61B 5/0408 600/382 |
| 6,865,409 | B2 | * | 3/2005 | Getsla | A61N 1/0452 128/902 |
| 8,750,959 | B2 | * | 6/2014 | Lindberg | A61B 5/0245 600/386 |
| 8,755,859 | B2 | * | 6/2014 | Lang | A61B 5/0408 600/372 |
| 9,510,762 | B2 | * | 12/2016 | Datovech | A61B 5/04085 |
| 2003/0220553 | A1 | * | 11/2003 | Axelgaard | A61B 5/04087 600/391 |

FOREIGN PATENT DOCUMENTS

| | | |
|---|---|---|
| JP | 2013248139 | 12/2013 |
| JP | 2014042707 | 3/2014 |
| JP | 2014200559 | 10/2014 |

* cited by examiner

BIOLOGICAL ELECTRODE TOOL

TECHNICAL FIELD

The present invention relates to a biological electrode tool for acquiring biological signals, such as a vital sensor for obtaining an electrocardiogram and the like.

BACKGROUND ART

Bioelectricity generated by a living body, such as a human body, is induced by the activity of the heart, the brain, muscles and the like. A weak voltage produced by the induced bioelectricity can be acquired using a biological electrode tool closely attached to the skin of the living body. The acquisition may be temporary in the case of an electrocardiogram for health checkup, or may continue for a long time in the case of a surgery or health management for healthcare, for example. Accordingly, the state of the heart and the like is diagnosed in accordance with the data to be acquired.

The biological electrode tool typically includes an electrode portion which is attached to the living body to acquire the biological signal, and a lead portion for externally leading the biological signal from the electrode portion (see Patent Documents 1 and 2).

It is desirable that the biological electrode tool is able to fit the skin so as to feel natural and comfortable. Accordingly, it has been proposed to cover the entire areas of the upper and lower surfaces of the electrode portion, except for the portion that contacts the living body, with nonwoven fabric, and to also cover the entire areas of the upper and lower surfaces of the lead portion, except for an external lead-out end portion thereof, with nonwoven fabric (see Patent Document 2, paragraphs 0021 to 0022, and FIG. 1 and FIG. 3).

CITATION LIST

Patent Literatures

Patent Document 1: JP-05-36402 Y
Patent Document 2: JP-A-2014-200559

SUMMARY

Problems to be Solved by the Invention

The biological electrode tool including the electrode portion and the lead portion with the upper and lower surfaces thereof covered with the nonwoven fabric may be manufactured by stamping out a biological electrode portion and a lead portion in a plurality of patterns of the biological electrode portion and the lead portion formed on a film (see Patent Document 2, paragraph 0025, and FIG. 4 to FIG. 7).

In this case, a conductive electrode and a conductive lead wire are exposed on the end faces of the stamped-out electrode portion and lead portion. When the exposed conductive portions contact the skin and the like, the detection signal may become unstable and an error may be caused. In addition, the living body (human) may feel uncomfortable.

The lead portion may be as long as 1 m or longer. In this case, the influence of external noise may have to be considered, because the external noise may affect detection accuracy and cause an error.

In light of the above circumstance, a first object of the present invention is to eliminate the exposure of the conductive portion. A second object is to eliminate the influence of external noise.

Solution to the Problems

In order to achieve the first object, according to the present invention, full circumferential peripheries of the nonwoven fabrics on the upper and lower surfaces of the electrode portion and the lead portion are bonded except for the portion that contacts the living body and the external lead-out end portion. According to this configuration, neither the electrode of the electrode portion nor the thin-film lead wire of the lead portion are exposed. Accordingly, the instability in detection signal or an error caused thereby due to the contact of the exposed conductive portion with the skin and the like can be prevented. Further, the living body, such as a human, is prevented from feeling uncomfortable.

In order to achieve the second object, the biological electrode tool according to the present invention is configured to shield external noise by means of a shield layer provided around the lead wire on the entire circumferential surface of the lead portion via an insulating layer. The shield layer may also be provided in the electrode portion. In this case, it goes without saying that the portion that contacts the living body is excluded.

As a configuration of the present invention to achieve the first object, the configuration including: an electrode portion attached to a living body to acquire a biological signal; and a lead portion for externally leading out the biological signal from the electrode portion can be employed. In the configuration, the electrode portion can include an electrode having upper and lower surfaces entire areas of which are covered with a nonwoven fabric having an electrode opening portion on a living body contacting side, and with a nonwoven fabric opposing the nonwoven fabric; the lead portion can also include upper and lower surfaces entire areas of which are covered with the nonwoven fabrics, except for an external lead-out end portion; the nonwoven fabrics on the upper and lower surfaces of the electrode portion and the lead portion can include bonding portions in full circumferential peripheries of the nonwoven fabrics, the bonding portions being bonded via an adhesive layer except for the electrode opening portion and the external lead-out end portion.

In this configuration, the shield layer is provided along the entire length of the lead portion, covering the entire circumference of the lead wire via the insulating layer. The entire area of the shield layer is covered with the nonwoven fabrics. The nonwoven fabrics are bonded in the bonding portion via the adhesive layer. In this way, the shield layer is also prevented from being exposed from the nonwoven fabrics on the upper and lower surfaces. Accordingly, the second object is achieved.

The shield layer makes it possible to send the biological signal obtained by the electrode portion to the measurement equipment while minimizing the entry of external noise. Accordingly, an increase in S/N is achieved, which eliminates the need for a means for increasing S/N. As a result, the cost of the device as a whole can be decreased. In addition, the shield layer is not exposed, either. Accordingly, the living body can be prevented from feeling uncomfortable due to contact.

The nonwoven fabric on the living body contacting side may be coated with adhesive resin, whereby the lead portion can be closed attached to the living body.

The thin-film lead wire may be obtained by forming a metal foil or a vapor-deposited film of Cu (copper), Au (gold), Ag (silver), Al (aluminum), or Ni (nickel), for example, on a sheet (or film) shaped base material. The lead wire may also be manufactured by forming an electrically conductive ink, electrically conductive paste, or electrically conductive adhesive, obtained by dispersing an electrically conductive polymer or electrically conductive filler in a binder, on a sheet-shaped base material. Examples of the electrically conductive polymer that may be used include polyacetylene, polypyrrole, polythiophene, and polyaniline. Examples of the electrically conductive filler include electrically conductive metal powders, such as Cu powder, Ag powder, Au powder, Al powder, and Ni powder. It is also possible to use an electrically conductive filler obtained by plating or coating an electrically conductive material on a core material of the metal powder or resin powder. It is also possible to use a carbon powder or an electrically conductive polymer powder and the like as the electrically conductive filler.

The thickness and width of the thin-film lead wire may be determined arbitrarily as long as its function can be exerted. For example, the thickness may range from 1 to 100 μm, and the width may range from 100 to 5000 μm. It is also possible to apply, for example, a material which includes an electrically conductive material with a diameter of 20 to 100 μm, such as extra-fine copper wire (high-strength wire), carbon nanotube, or metal-plated resin fiber, and which can be molded into a thin shape or a narrow shape, as appropriate. In the present invention, these may also be included in the thin-film lead wire.

Any nonwoven fabric may be used as long as the nonwoven fabric does not have electrically conductivity. For example, polyester resin fiber may be used. The thickness is not particularly limited as long as it does not adversely affect the use of the fabric. For example, the thickness may range from 50 to 3000 μm.

The adhesive material for bonding the upper and lower nonwoven fabrics preferably has high adhesion to the interposed conductive material (electrode, lead wire). More preferably, the adhesive has electric insulation property and/or waterproof property. For example, polyethylene (PE) may be used.

The shield layer may be formed from the same material and by the same method as for the thin-film lead wire. The thickness may also be arbitrarily determined as long as the shield effect can be obtained. The thickness, for example, may range from 0.1 to 1000 μm.

Effects of the in Invention

The present invention has the above-described configurations. Accordingly, a biological electrode tool that is comfortable to the skin and that has high detection accuracy can be obtained.

BRIEF DESCRIPTION OF THE DRAWINGS

Figure 1:
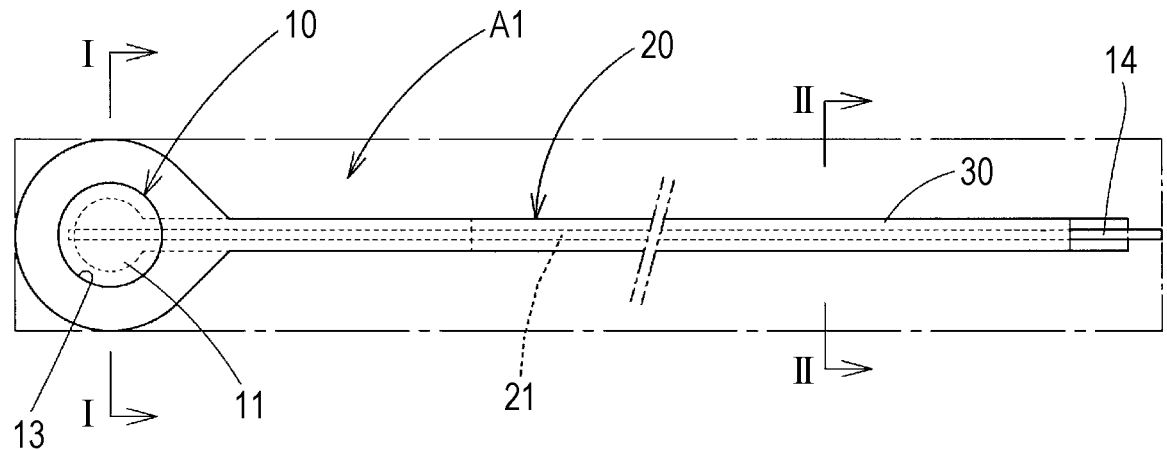
FIG. 1 is a plan view of a biological electrode tool according to an embodiment of the present invention, with an intermediate portion thereof omitted.
Figure 2A:
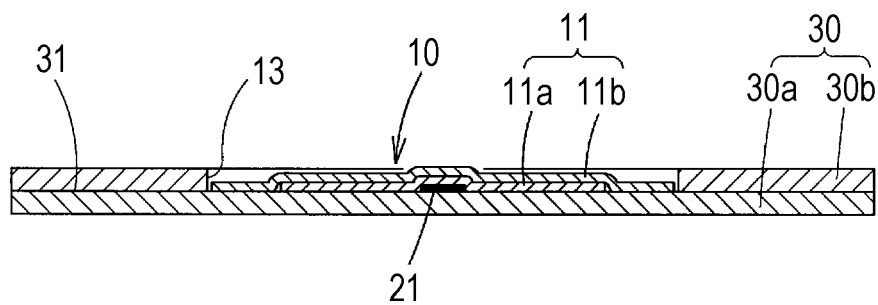
FIG. 2A is a cross sectional view along line I-I of FIG. 1.
Figure 2B:
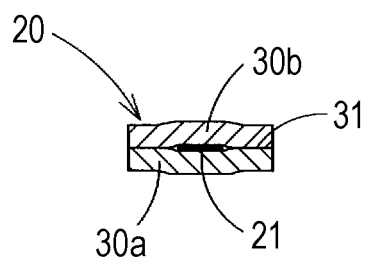
FIG. 2B is a cross sectional view along line II-II of FIG. 1.
Figure 3:
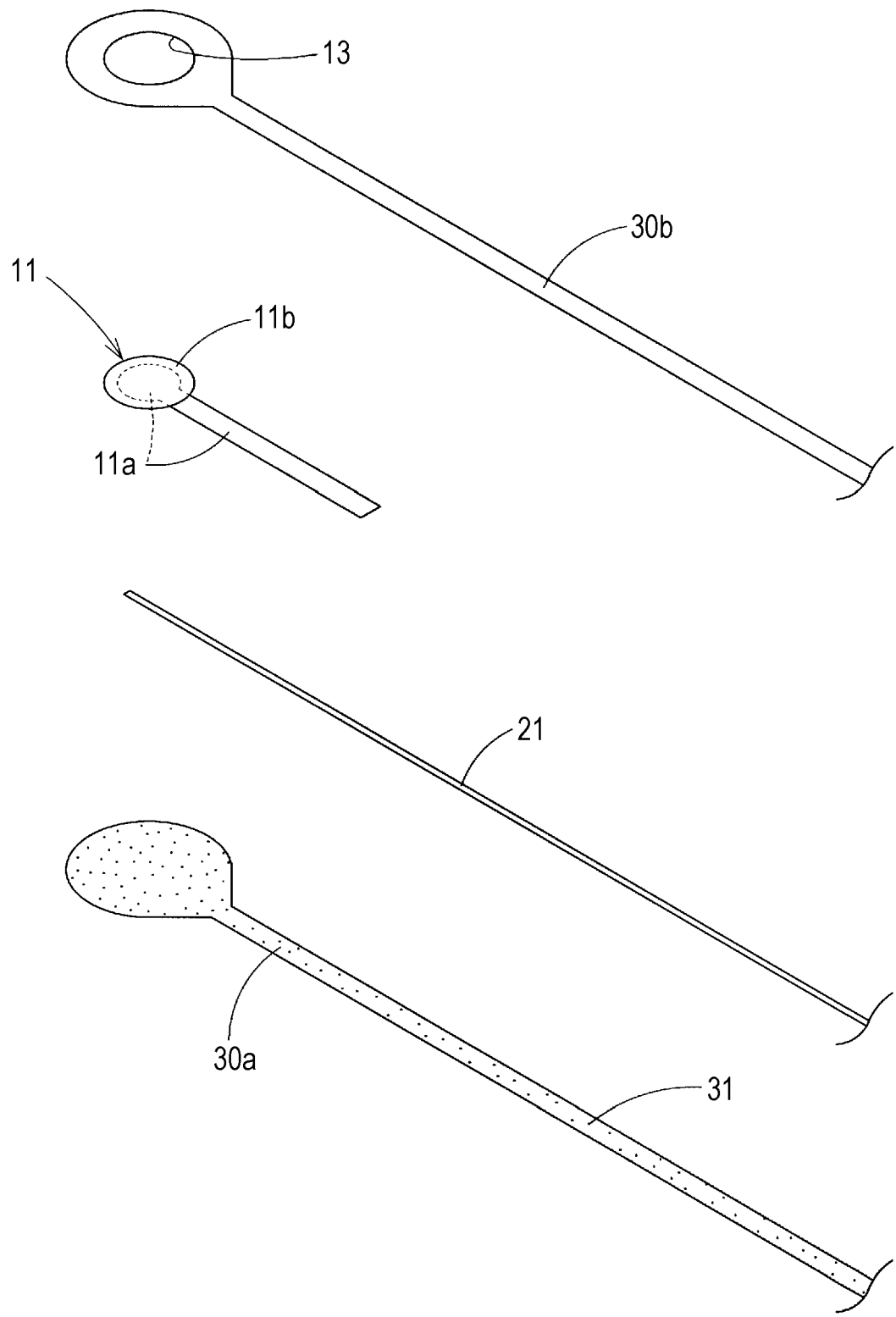
FIG. 3 is a partially exploded perspective view of the embodiment.

FIG. 1 to FIG. 4C illustrate a biological electrode tool according to an embodiment of the present invention. The biological electrode tool A1 includes, as is conventional, an electrode portion 10 which is attached to a living body, such as a human body, to acquire a biological signal, and a lead portion 20 for leading the biological signal out of the electrode portion 10. The entire areas of upper and lower surfaces of the electrode portion 10 are covered with a nonwoven fabric 30, except for a portion thereof (electrode opening portion) that contacts the living body. The entire areas of upper and lower surfaces of the lead portion 20 is also covered with the nonwoven fabric 30, except for an external lead-out end portion. Full circumferential peripheries of the nonwoven fabric 30 of the upper and lower surfaces of the electrode portion 10 and the lead portion 20 are bonded to each other, except for the portion contacting the living body and the external lead-out end portion.

The electrode portion 10 includes an electrode 11 including an Ag paste layer 11a and a silver chloride (AgCl) paste layer 11b which are successively disposed on the nonwoven fabric 30.

The lead portion 20 includes a copper foil electric wire 21 disposed on the nonwoven fabric 30. The copper foil electric wire (lead wire) 21 includes, for example, a copper foil electric wire (see FIG. 4A) obtained by attaching a copper foil 21b (with a thickness of 6 μm, for example) onto a wide polyethylene terephthalate (PET) film 21a (with a thickness of 12 μm, for example), and cutting into a 1 mm width section.

Figure 4A:
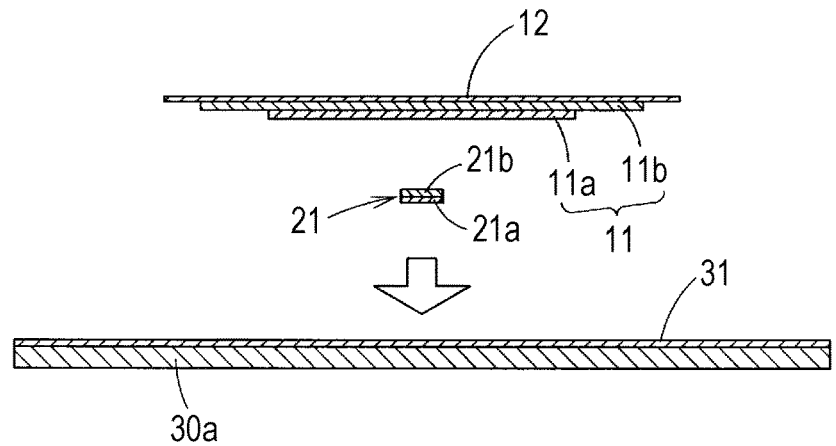
FIG. 4A is an explanatory diagram illustrating the manufacture of the embodiment.
Figure 4B:
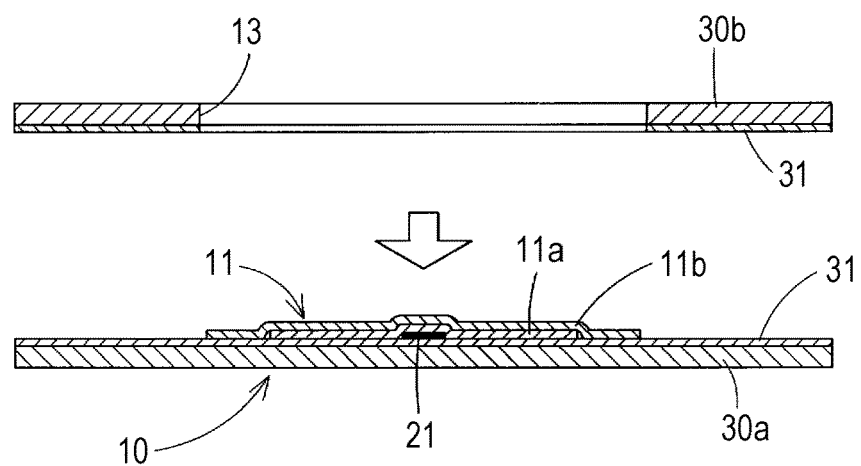
FIG. 4B is another explanatory diagram illustrating the manufacture.
Figure 4C:
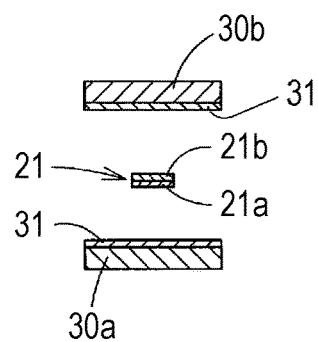
FIG. 4C is another explanatory diagram illustrating the manufacture.

On opposing surfaces of the upper and lower nonwoven fabrics 30 (hereafter, in FIG. 4B and FIG. 4C, the lower (back side) nonwoven fabric will be referenced at 30a, and the upper (front side) nonwoven fabric at 30b), an adhesive layer 31 (with a thickness of 20 μm, for example) including an attached PE film or a PE coating is formed as adhesive material. The adhesive layer 31 ensures insulation property and waterproof property. Accordingly, any sweat or various liquids that may become attached to the nonwoven fabric 30 does not adversely affect the living body. In addition, the influence on detection accuracy is minimized.

The biological electrode tool A1 having the above configuration may be manufactured as follows. First, as illustrated in FIG. 4A, a member is prepared which includes a PET film 12 and the AgCl paste layer 11b and the Ag paste layer 11a of required sizes successively disposed on the film. Then, on the nonwoven fabric 30a with the adhesive layer 31 formed thereon, the copper foil electric wire 21 is placed with the PET film 21a facing the nonwoven fabric 30a. On top of the copper foil electric wire 21, the layers of the Ag paste layer 11a and the AgCl paste layer 11b are stacked. As illustrated in FIG. 4B and FIG. 4C, onto the nonwoven fabric 30a, there is transferred the electrode 11 including the Ag paste layer 11a and the AgCl paste layer 11b with the electric wire 21 interposed therebetween and via the adhesive layer 31, by dry laminating method or thermal transfer method, for example. The Ag paste layer 11a may be obtained by mixing an Ag filler in an adhesive resin.

Then, the nonwoven fabric 30b including a hole (a portion that contacts the living body; the electrode opening portion) 13 of a size corresponding to the electrode 11 is thermally fused (thermally adhered) with the lower nonwoven fabric 30a via the adhesive layer 31, with the electrode 11 positioned in the hole 13 (see FIG. 4B, FIG. 4C, FIG. 2A, and FIG. 2B).

In this case, the nonwoven fabric 30 (the nonwoven fabrics 30a, 30b) may be cut into the shape indicated by solid lines in FIG. 1. The nonwoven fabric 30 may also be a member obtained by cutting out bonded and elongated nonwoven fabrics 30a, 30b, indicated by dot-dash-lines, into the shape indicated by the solid lines. In either case, the nonwoven fabric 30 (30a, 30b) of the upper and lower surfaces of the electrode portion 10 and the lead portion 20 are set to be wider than the diameter of the circular electrode 11 or the width of the electric wire 21. The peripheries of the nonwoven fabrics 30a, 30b except for the portion that contacts the living body (the hole 13) and the external lead-out end portion (the terminal portion 14) form bonding portions. Full circumferential peripheries of the nonwoven fabrics 30a, 30b are bonded via the adhesive layer 31 in the bonding portions (see FIG. 2A and FIG. 2B). Accordingly, neither the electrode 11 of the electrode portion 10 nor the electric wire 21 of the lead portion 20 are exposed. Thus, the electrode 11 and the electric wire 21, i.e., the conductive portions, do not come into contact with the skin except for the portion that contacts the living body.

The biological electrode tool A1 according to the embodiment can be used to obtain an electrocardiogram and the like by, as is conventionally done, attaching the electrode portion 10 to a required position of the human body via electrically conductive gel, and connecting examination equipment (measurement equipment), such as cardiography equipment, to the terminal portion 14.

Figure 5:
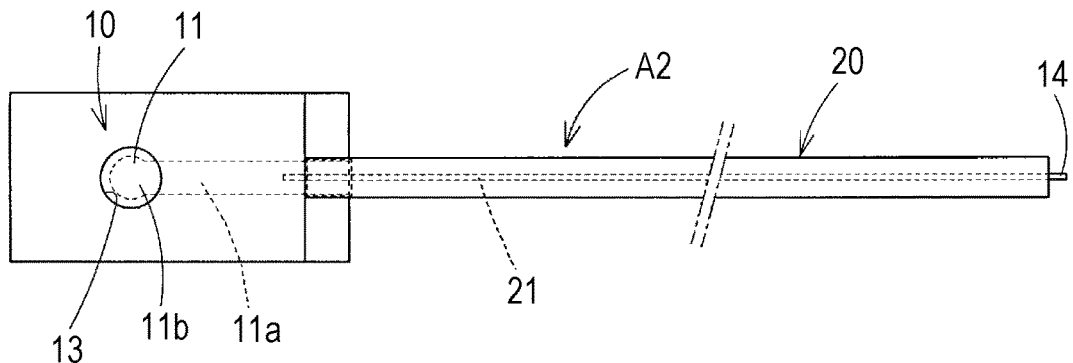
FIG. 5 is a plan view of a biological electrode tool according to a second embodiment, with the intermediate portion being omitted.
Figure 6:
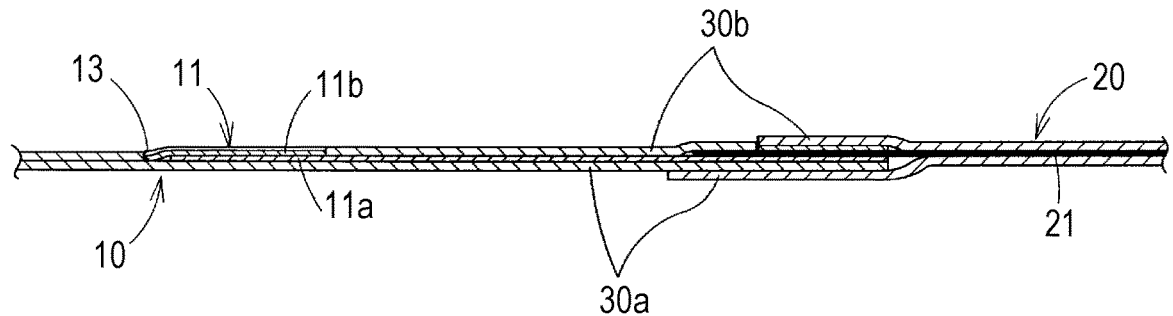
FIG. 6 is a partial longitudinal cross sectional view of the second embodiment.
Figure 7:
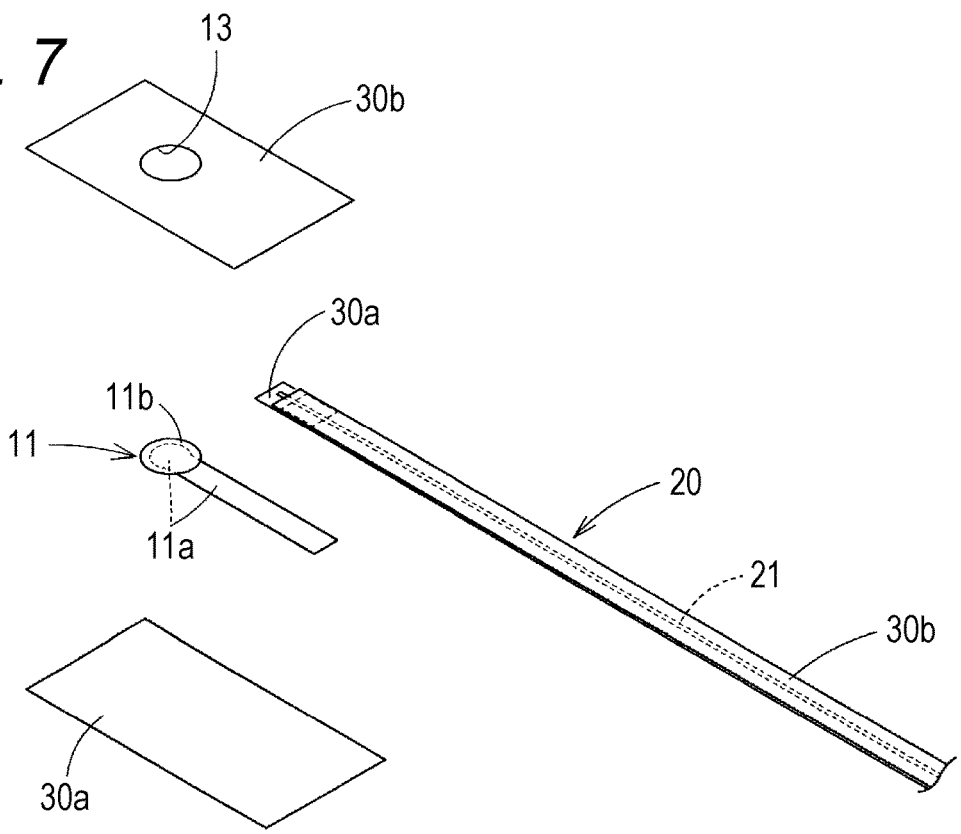
FIG. 7 is a partially exploded perspective view of the second embodiment.

FIG. 5 to FIG. 7 illustrate a biological electrode tool A2 according to a second embodiment. The biological electrode tool A2 includes the electrode portion 10 and the lead portion 20 which are separately manufactured. The configurations and the like of the electrode 11 and the electric wire 21 are similar to those of the previous embodiment. The electrode portion 10 and the lead portion 20 are connected by, as illustrated in FIG. 6 and FIG. 7, bonding the upper nonwoven fabric 30b of the electrode portion 10 to the lower nonwoven fabric 30a after the electric wire 21 of the lead portion 20 is placed on a lead-out portion of the Ag paste layer 11a. Then, in this state, the upper nonwoven fabric 30b is thermally fused with the lower nonwoven fabric 30a for bonding.

The biological electrode tool A2 according to the second embodiment can also be used to obtain an electrocardiogram and the like by, as is conventionally done, attaching the electrode portion 10 to a required position of the human body via electrically conductive gel, and connecting the examination equipment, such as cardiography equipment, to the terminal portion 14.

Figure 8:
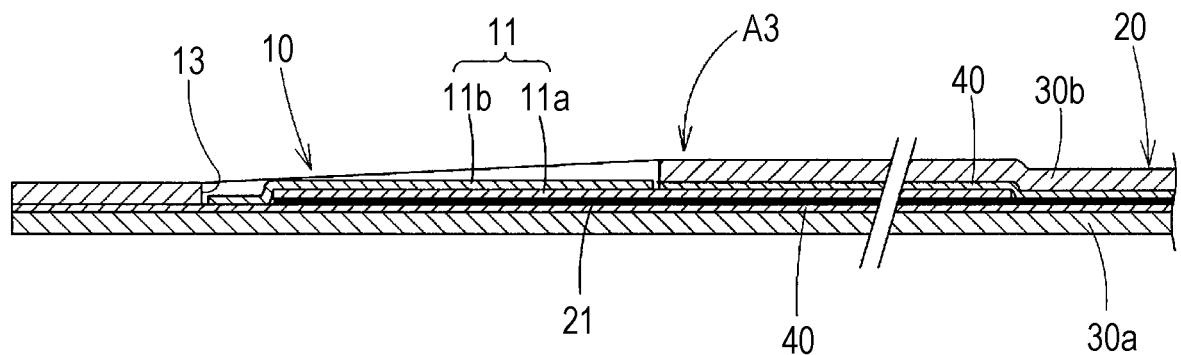
FIG. 8 is a partial longitudinal cross sectional view of a third embodiment.
Figure 9A:
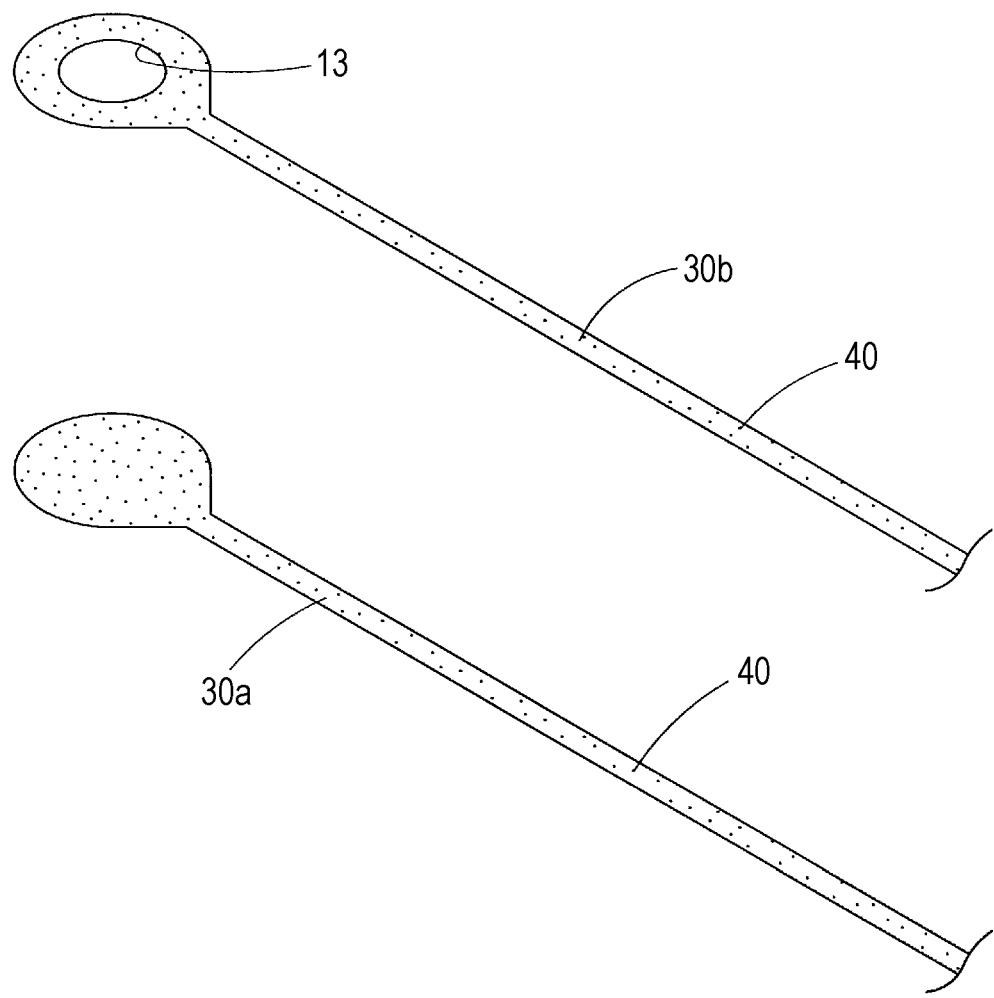
FIG. 9A is an explanatory diagram illustrating the manufacture of the third embodiment, which is also an exploded perspective view of the nonwoven fabric portion, where an upper surface-side nonwoven fabric is turned upside down.
Figure 9B:
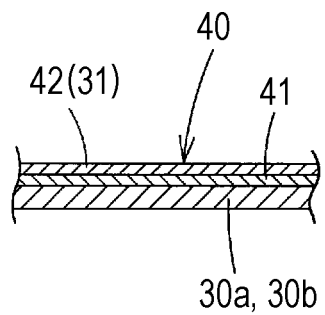
FIG. 9B is a cross sectional view of the nonwoven fabric according to the third embodiment.

FIG. 8, FIG. 9A, and FIG. 9B further illustrate a biological electrode tool A3 according to a third embodiment. The biological electrode tool A3 is provided with a shield layer 40 that covers the electrode 11 and the electric wire 21 along the entire circumference of the electrode portion 10 except for the hole 13 thereof, and the entire length of the lead portion 20. The entire area of the shield layer 40 is covered with the nonwoven fabrics 30a, 30b on the upper and lower surfaces. The nonwoven fabric is bonded at the bonding portion via the adhesive layer 31. Accordingly, the shield layer 40 is also formed so as not to expose the side ends thereof.

During the formation of the shield layer 40, an electrically conductive layer 41 is provided on the opposing surfaces of the nonwoven fabrics 30a, 30b by coating or attachment of foil, for example. The electrically conductive layer 41, as in the case of the electric wire 21, is provided by a metal foil of Cu, Au, Ag, Al, or Ni; a vapor-deposited film thereof; or an electrically conductive ink, an electrically conductive paste, or an electrically conductive adhesive including an electrically conductive resin or an electrically conductive filler dispersed in a binder. The electrically conductive layers 41 are bonded via an insulating layer 42 including an insulating adhesive 31 of PE, for example. In this case, the insulating layer 42 is at least provided in an area in which the electrically conductive layer 41 may potentially contact the electric wire 21 or the electrode 11 (and not necessarily in the entire areas of the opposing surfaces of the nonwoven fabrics 30a, 30b as illustrated in FIG. 9A).

The biological electrode tool A3 according to the third embodiment can also be used to obtain an electrocardiogram and the like by, as is conventionally done, attaching the electrode portion 10 to a required position of the living body via electrically conductive gel, and connecting the examination equipment, such as cardiography equipment, to the terminal portion 14. In this case, the shield layer 40 provided around the electrode portion 10 and the entire length of the top and bottom of the electric wire 21 shields external noise, whereby detection accuracy is improved.

The shield layer 40 may be provided only on the lead portion 20 (and may not be provided on the electrode portion 10).

The lead wire (electric wire) 21 and the shield layer 40 may be formed by directly coating the nonwoven fabric 30 with an electrically conductive paste and the like. The biological electrode tools A1 to A3 may be configured to include electrically conductive gel provided on the AgCl layer 11b. In this case, a film provided so as to cover the electrically conductive gel may be removed in use.

The living body side of the nonwoven fabric 30a of the lead portion 20 may be coated with an adhesive resin of urethane resin or acrylic resin and the like, whereby the lead portion 20 can be closely attached to the living body. As a result, the handling of the biological electrode tools A1 to A3 may be improved when attached for a long time, such as for a full day. It goes without saying that the living body includes not only human bodies but also animals such as dogs and cats.

The currently disclosed embodiments are to be considered illustrative in all aspects and are not limiting. It is intended that the scope of the present invention is defined by the appended claims, and that the present invention includes all modifications falling within the scope of the claims and equivalents thereof.

LIST OF REFERENCE NUMERALS

10 Electrode portion
11 Electrode
11a Ag paste layer
11b AgCl paste layer
12 PET film
13 Hole in a portion that contacts the living body (living body contacting portion)
14 Terminal portion (external lead-out portion)
20 Lead portion
21 Lead wire (electric wire)
30 Nonwoven fabric
30a Lower (rear) nonwoven fabric
30b Upper (front) nonwoven fabric
31 Adhesive layer
40 Shield layer
41 Metal layer forming a shield layer
42 Insulating layer

The invention claimed is:

1. A biological electrode tool comprising:
an electrode portion (10) adapted to be attached to a living body to acquire a biological signal; and
a lead portion (20) for externally leading out the biological signal from the electrode portion (10);
wherein:
the electrode portion (10) includes an electrode (11) having upper and lower surfaces entire areas of which are covered with a first nonwoven fabric (30b) having an electrode opening portion (13) on a living body contacting side, and with a second nonwoven fabric (30a) opposing the first nonwoven fabric (30b);
the lead portion (20) also includes upper and lower surfaces entire areas of which are covered with the first and second nonwoven fabrics (30a, 30b), except for an external lead-out end portion (14);
the first and second nonwoven fabrics (30a, 30b) on the upper and lower surfaces of the electrode portion (10) and the lead portion (20) include bonding portions in full circumferential peripheries of the first and second nonwoven fabrics, the bonding portions being bonded via an adhesive layer (31) except for the electrode opening portion (13) and the external lead-out end portion (14);
the lead portion (20) comprises a lead wire (21) placed on the second nonwoven fabric;
in a cross sectional view of the electrode portion, the lead wire is sandwiched between the second nonwoven fabric and the electrode;
the adhesive layer (31) has electric insulation property and/or waterproof property; and
the electrode (11) comprises:
a silver chloride layer having a first circular shape; and
a silver layer including a first portion having a second circular shape with a diameter smaller than a diameter of the first circular shape, and a lead-out portion extending from the first portion and protruding from the silver chloride layer in a direction toward the external lead-out end portion (14), the first portion of the silver layer being in direct contact with the silver chloride layer.

2. The biological electrode tool according to claim 1, comprising a shield layer (40) covering the entire circumference of the lead wire (21) via an insulating layer (42) along the entire length of the lead portion (20),
wherein:
the shield layer (40) has an entire area thereof covered with the first and second nonwoven fabrics (30a, 30b); and
the first and second nonwoven fabrics (30a, 30b) are bonded at the bonding portions via the adhesive layer (31).

3. The biological electrode tool according to claim 2, wherein the first nonwoven fabric (30b) on the living body contacting side is coated with an adhesive resin.

4. The biological electrode tool according to claim 1, wherein the first nonwoven fabric (30b) on the living body contacting side is coated with an adhesive resin.

5. The biological electrode tool according to claim 1, wherein
the silver layer is placed over the second nonwoven fabric and the lead wire; and
the silver chloride layer is placed over the first portion of the silver layer.

6. The biological electrode tool according to claim 1, wherein the lead wire comprises:
a base material facing the second nonwoven fabric; and
a metal foil or a vapor-deposited film of a metal on the base material.

7. The biological electrode tool according to claim 1, wherein the lead wire comprises:
a base material facing the second nonwoven fabric; and
an electrically conductive ink, paste or adhesive on the base material.

8. The biological electrode tool according to claim 1, wherein the adhesive layer (31) has waterproof property.

* * * * *